United States Patent [19]

Hahn

[11] Patent Number: 5,213,434
[45] Date of Patent: May 25, 1993

[54] WORK DEVICE SHAFT FOR THE ELECTRIC DRIVE MECHANISM OF A TOOTHBRUSH

[75] Inventor: Matthias Hahn, Frankfurt, Fed. Rep. of Germany

[73] Assignee: Rowenta-Werke GmbH, Offenbach am Main, Fed. Rep. of Germany

[21] Appl. No.: 789,367

[22] Filed: Nov. 8, 1991

[30] Foreign Application Priority Data

Nov. 29, 1990 [DE] Fed. Rep. of Germany ....... 9016226

[51] Int. Cl.$^5$ ............................................. F16C 31/00
[52] U.S. Cl. ..................................... 403/59; 403/287; 403/122; 403/361; 15/22.1; 15/28; 74/99 R
[58] Field of Search ..................... 15/167.1, 22.2, 22.1, 15/28; 403/122, 361, 289, 59, 287; 74/99 R, 108

[56] References Cited

U.S. PATENT DOCUMENTS

| | | | |
|---|---|---|---|
| 3,182,345 | 5/1965 | Smith | 403/361 X |
| 3,214,776 | 11/1965 | Bercourz | 74/99 |
| 4,281,987 | 8/1981 | Kleesattel | 15/28 X |
| 4,811,445 | 3/1989 | Lagieski et al. | 403/361 X |
| 4,827,550 | 5/1989 | Graham et al. | 15/22.1 |
| 4,989,287 | 2/1991 | Scherer | 15/22.1 |
| 5,044,035 | 9/1991 | Barradas | 15/22.2 X |
| 5,077,855 | 1/1992 | Ambasz | 15/22.2 X |

FOREIGN PATENT DOCUMENTS 9113570  9/1991  World Int. Prop. O. ........... 15/22.2

Primary Examiner—Andrew V. Kundrat
Assistant Examiner—Harry C. Kim
Attorney, Agent, or Firm—Anderson Kill Olick & Oshinsky

[57] ABSTRACT

A plug-in connector for an electric toothbrush drive mechanism, including an electric motor and a movement converter which is arranged between the motor and a plug-in shaft and sets the plug-in shaft in radial and longitudinal movement, the motor and converter being arranged in a housing, and the plug-in shaft, which is supported in a bottom surface of the housing, has a free end that penetrates the bottom surface, the plug-in connector is detachably connected with the housing and the plug-in shaft is engaged in an installed state with a connecting rod arranged on the inside of the plug-in connector, and an end of the connecting rod remote of the plug-in shaft is in a working connection with a radial drive, the connecting rod and radial drive being connected with one another by an elastically deformable spiral, and the connecting rod, spiral and radial drive being constructed so as to form one piece.

3 Claims, 1 Drawing Sheet

WORK DEVICE SHAFT FOR THE ELECTRIC DRIVE MECHANISM OF A TOOTHBRUSH

BACKGROUND OF THE INVENTION

The invention is directed to a plug-in connector for an electric toothbrush drive mechanism including an electric motor and a movement converter which is arranged between the motor and the plug-in shaft and sets the plug-in shaft in radial and longitudinal movement. The motor and converter are arranged in a housing, and the plug-in shaft, which is supported in a bottom surface of the housing, penetrates the bottom surface with its free end. The plug-in connector is detachably connected with the housing, and the plug-in shaft engages in the installed state with a connecting rod arranged in the interior of the plug-in connector, and the end of the connecting rod remote from the plug-in shaft is in a working connection with a radial drive.

An electric toothbrush comprising a drive mechanism consisting of an electric motor and a movement converter arranged between the motor and the plug-in shaft, as well as a brush body constructed as a plug-in connector, is known from EP-OS 0 357 863. The movement converter imparts upon the plug-in shaft both radial and longitudinal movement. The motor and the movement converter are arranged in a housing. In the installed state, the plug-in connector is rotatably connected with the housing of the toothbrush drive mechanism. A connecting rod is supported in the plug-in connector so that the connecting rod can execute only longitudinal movements, but not radial movements. The connecting rod is detachably connected via a catch connection with the plug-in shaft of the electric drive mechanism. A plurality of brushes are supported in the plug-in connector and are set in radial movement by the connecting rod by means of an eccentric drive. During operation, the movement of the plug-in shaft is transmitted so that the entire plug-in connector executes radial movements, while the longitudinal movements of the connecting rod allow the brushes to execute radial movements in addition after conversion at the eccentric drive. Since the entire plug-in connector, i.e. the housing and brushes, as well as the brushes can execute additional radial movements, these radial movements make it impossible to clean the intermediate spaces between the teeth or to polish the teeth even when only one brush is arranged. Moreover, the expenditure of energy for the drive mechanism is very high and is increased still further because of the soiling of the catch connection between the drive mechanism and plug-in connector due to toothpaste.

SUMMARY OF THE INVENTION

The object of the invention is to expand the area of use of an electric toothbrush drive while avoiding the aforementioned disadvantages by means of a simple added device, by means of which the teeth can be polished and the spaces between the teeth can be cleaned, wherein the polishing and/or cleaning device exclusively executes radial movements.

Pursuant to this object, and others which will become apparent hereafter, one aspect of the present invention resides in a plug-in connector in which the connecting rod and the radial drive are connected with one another by an elastically deformable spiral. Also, the connecting rod, spiral and radial drive are constructed to form one piece.

Accordingly, the area of use of an electric toothbrush drive is expanded by means of the plug-in connector according to the invention. In addition to conventional plug-in toothbrushes, which advantageously execute a radial and longitudinal movement, devices, e.g. for polishing the teeth or cleaning the spaces between the teeth, which execute exclusively radial movements can be driven by the same drive mechanism.

In operation, the connecting rod which is supported in the interior of the plug-in connector, according to the invention, is in working connection with the plug-in shaft of the drive mechanism at one end and with the radial drive for a tooth treatment tool at its end remote from the plug-in shaft. The plug-in shaft of the drive mechanism executes a radial and longitudinal movement. The radial movement of the plug-in shaft is rendered ineffective in the connecting rod according to the invention, while the longitudinal movement of the plug-in shaft is transmitted by the connecting rod. The longitudinal movement of the connecting rod acts on a radial drive arranged in the plug-in connector, the longitudinal movement being converted into a radial movement in the radial drive.

A polishing and/or cleaning device constructed as a plug-in connector is driven via the radial drive and executes exclusively radial movements. The end of the connecting rod which is in a working connection with the radial drive is advantageously constructed in a spiral-shaped manner and the spiral encloses the radial drive supported in the plug-in connector. A large longitudinal movement of the connecting rod can be converted into a large radial movement in a minimum of space by means of the elastically deformable spiral. The connecting rod, spiral and radial drive are advantageously constructed so as to form one piece and be elastically deformable, so that this structural component part can be simply and inexpensively produced, e.g. as a plastic injection molded part.

In order to cancel the radial movement of the plug-in shaft of the drive mechanism so that only its longitudinal movement acts on the radial drive arranged in the plug-in connector, a ball-and-socket joint can be arranged between the plug-in connector and the connecting rod in another embodiment. It is particularly advantageous to arrange the ball at the free end of the plug-in shaft and the socket belonging to the ball at the end of the connecting rod, wherein the ball diameter is equal to or less than the diameter of the plug-in shaft. Accordingly, it is possible to bring the socket and ball into a working connection by means of a simple plugging together, while the ball itself does not obstruct the connection between the toothbrush and plug-in shaft.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE PREFERRED EMBODIMENTS

Figure 1:
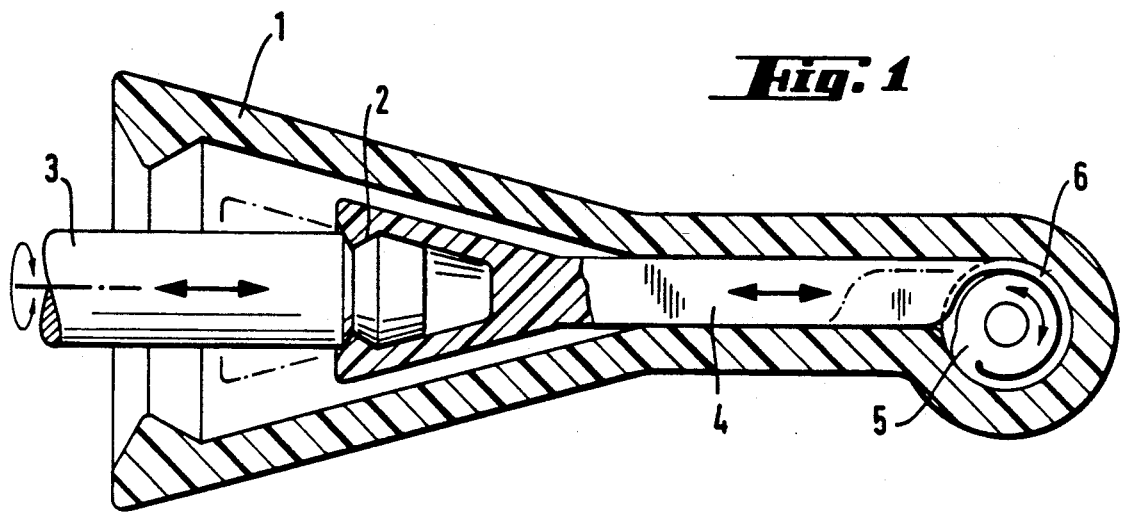
FIG. 1 shows a plug-in connector according to the invention, in longitudinal section.

FIG. 1 shows a plug-in connector 1, according to the invention, which is detachably supported, by means of a catch connection 2, on a plug-in shaft 3 of an electric toothbrush drive, not shown. A connecting rod 4 and a radial drive 5 for a tooth treatment tool are supported in the plug-in connector 1. The connecting rod 4 is in a working connection with the radial drive 5 via a formed on elastically deformable spiral 6. The connecting rod 4, radial drive 5 and spiral 6 are constructed so as to form one piece and be elastically deformable. During operation, the plug-in shaft 3 executes a radial and longitudinal movement. The radial movement is rendered ineffective in the connecting rod, while the longitudinal movement of the plug-in shaft 3 is transmitted to the radial drive 5 via the connecting rod 4 and the spiral 6. The longitudinal movement of the connecting rod 4 is converted in the radial drive 5 into a radial movement for the drive of a tooth treatment device, not shown. In an advantageous manner, the tooth treatment device can be connected with the radial drive 5 by being plugged-in.

Figure 2:
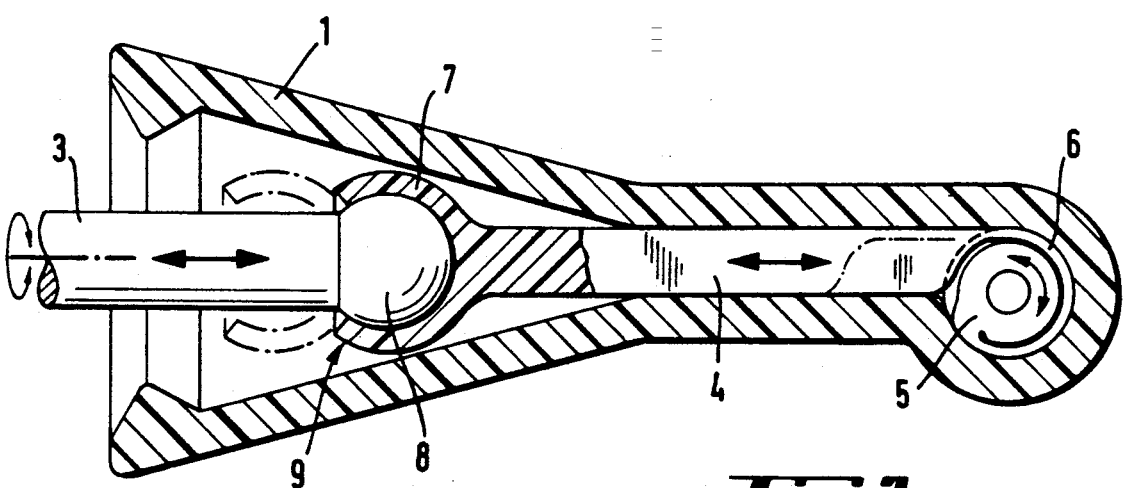
FIG. 2 shows another embodiment of the plug-in connector according to the invention, in longitudinal section.

FIG. 2 shows another embodiment form of the plug-in connector 1 according to the invention. In this construction, the end of the connecting rod 4 remote of the spiral 6 is constructed as a semicircular bearing shell 7 and the respective end of the plug-in shaft 3 is constructed as a ball 8. In operation, the connecting rod 4 is connected with the plug-in shaft 3 via the ball-and-socket joint 9 formed from the ball 8 and the bearing shell 7. The radial movement of the plug-in shaft 3 is rendered ineffective in the ball-and-socket joint 9. In this embodiment, the connecting rod 4, bearing shell 7, spiral 6 and radial drive 5 are constructed in one piece so as to be elastically deformable. Accordingly, the semicircular bearing shell 7 acts simultaneously as a snap-in connection between the connecting rod 4 and the plug-in shaft 3.

While the invention has been illustrated and described as embodied in a plug-in connector for an electric toothbrush drive mechanism, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims.

I claim:

1. A plug-in connector for use with an electric toothbrush having a tooth treatment tool and a drive with a plug-in shaft for imparting to the tooth treatment tool longitudinal and radial movements, said plug-in connector comprising a radial drive for imparting radial movement to the tooth treatment tool; and means for connecting the plug-in shaft of the toothbrush drive and said radial drive for converting a longitudinal movement of the plug-in shaft into a radial movement of said radial drive, said connecting means including a connecting rod attached, at one end thereof, to the plug-in shaft and, at another end thereof, to elastically deformable spiral means connected with said radial drive for converting the longitudinal movement of the plug-in shaft transmitted by said connecting rod to the radial movement of said radial drive, said connecting rod, said spiral means and radial drive being formed as an elastically deformable one-piece part.

2. A plug-in connector according to claim 1, wherein said spiral means is formed as a spirally shaped end of said connecting rod embracing said radial drive.

3. A plug-in connector according to claim 1, further comprising a ball and socket joint for attaching said one end of said connecting rod to the plug-in shaft.

* * * * *